US008304226B2

(12) United States Patent
Miller

(10) Patent No.: US 8,304,226 B2
(45) Date of Patent: *Nov. 6, 2012

(54) **QUALITY OF LIFE OF HEPATITIS C PATIENTS WITH A FORMULATION FOR ADMINISTRATION TO THE ORAL MUCOSA INCLUDING FREEZE DRIED LYSATE OF SELECTED *LACTOBACILLUS* OR *BIFIDOBACTERIUM* SPECIES AND N-ACETYL D-GLUCOSAMINE**

(76) Inventor: Carl Miller, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/449,905

(22) Filed: Apr. 18, 2012

(65) Prior Publication Data

US 2012/0201916 A1 Aug. 9, 2012

Related U.S. Application Data

(63) Continuation-in-part of application No. 13/180,779, filed on Jul. 12, 2011, which is a continuation of application No. 11/508,633, filed on Aug. 22, 2006, now Pat. No. 8,007,783.

(51) Int. Cl.
*A61K 35/66* (2006.01)
*A61K 35/74* (2006.01)
(52) U.S. Cl. .................. 435/252.9; 435/243; 435/252.1; 435/252.4; 424/400; 424/93.45
(58) Field of Classification Search .................. 424/400, 424/93.1, 93.45; 435/243, 252.1, 252.4, 435/252.9
See application file for complete search history.

(56) References Cited

U.S. PATENT DOCUMENTS

| 5,716,615 | A | 2/1998 | Cavaliere |
| 6,281,191 | B1 | 8/2001 | Slesarev et al. |
| 6,767,557 | B2 * | 7/2004 | Ulrich et al. .................. 424/497 |
| 2004/0129174 | A1 * | 7/2004 | Li et al. ...................... 106/162.8 |

OTHER PUBLICATIONS

Araki, K, Shinozaki, T, Irie, Y, Miyazawa Y; Trial of oral administration of *Bifidobacterium breve* for the prevention of rotavirus infections; Kansenshogaku Zasshi Apr. 1999; 73 (4):305-10. PubMed PMID:10356887 (Abstract).
Armuzzi, A, Cremonini, F., et al; The effect of oral administration of *Lactobacillus GG* on antibiotic-associated gastrointestinal side-effects during *Helicobacter pylori* eradication therapy; Aliment Pharmacol Ther 2001; 15:163-169.
Taina Arvola, Kirsi Laiho, et al; Prophylactic *Lactobacillus GG* Reduces Antibiotic-Associated Diarrhea in Children with Respiratory Infections: A Randomized Study; Pediatrics 1999; 104;e64.
Aso, Y., Akaza H., et al; Preventive effect of a *Lactobacillus casei* preparation on the recurrence of superficial bladder cancer in a double-blind trial. The BLP Study Group.; European Urology [1995,27(2):104-9] (Abstract).

Melanie Beausoleil, Nadia Fortier, et al; Effect of a fermented milk combining *Lactobacillus acidophilus* CL1285 and *Lactobacillus casei* in the prevention of antibiotic-associated diarrhea: a randomized, double-blind, placebo-controlled trial; Can J Gastroenterol vol. 21, No. 11, Nov. 2007.
Michael de Vrese, Petra Winkler, et al; Effect of *Lactobacillus gasseri* PA 16/8, *Bifidobacterium longum* Sp 0713, *B. bifidum* MF 2015 on common cold episodes: a dounle blind, randomized, controlled trial; Clinical Nutrition (2005) 24, 481-491.
Lorenzo Drago, Ph.D., Elena De Vecchi, M.S., et al; Activity of a *Lactobacillus acidophilus*-Based Douche for the Treatment of Bacterial Vaginosis; The Journal of Alternative and Complementary Medicine; vol. 13, No. 4, 2007, pp. 435-438.
E Furrie, S Macfarlane, A Kennedy, et al; Synbiotic therapy (*Bifidobacterium longum*/Synergy 1) initiates resolution of inflammation in patients with active ulcerative colitis: a randomised controlled pilot trial; Gut 2005; 54:242-249,Published by group.bmj.com.
Yoshitaka Hirose, Shinji Murosaki, et al; Daily Intake of Heat-Killed *Lactobacillus plantarum* L-137 Augments Acquired Immunity in Healthy Adults; The Journal of Nutrition 136:3069-3073, 2006.
Angela B. Hoyos, MD; Reduced Incidence of Necrotizing Enterocolitis Associated with Enteral Administration of *Lactobacillus acidophilus* and *Bifidobacterium infantis* to Neonates in an Intensive Care Unit; International Journal of Infectious Diseases, vol. 3, No. 4, 199-202, 1999.
Bengt Klarin, Marie-Louise Johansson, et al; Adhesion of the probiotic bacterium *Lactobacillus plantarum* 299v onto the gut mucosa in critically ill patients: a randomised open trial; Critical Care 2005, 9:R285-R293.
Bengt Klarin, Goran Molin, et al; Use of the probiotic *Lactobacillus plantarum* 299 to reduce pathogenic bacteria in the oropharynx of intubated patients: a randomised controlled open pilot study; Critical Care 2008, 12:R136.
Catherine Mullie, Asmae Yazourh, et al; Increased Poliovirus-Specific Intestinal Anibody Response Coincides with Promotion of *Bifidobacterium breve* in infants: A Randomized, Double-Blind, Placebo-Controlled Trial; Pediatric Research, vol. 56 No. 5, 2004, pp. 791-795.

(Continued)

*Primary Examiner* — Ruth Davis
(74) *Attorney, Agent, or Firm* — Gearhart Law, LLC

(57) ABSTRACT

Disclosed are quick dissolve tablets, each including freeze dried lysate of *Lactobacillus reuteri, Lactobacillus casei, Lactobacillus plantarum, Llactobacillus rhamnosus* GG, *Lactobacillus acidophilus, Bifidobacterium bifidium, Bifidobacterium longum, Bifidobacterium infantis* or *Bifidobacterium breve* and N-acetyl-glucosamine (NAG), as well as excipients, for oral mucosal administration, for improving the quality of life of Hepatitis C patients. Any formulation suitable for oral mucosal administration can be employed for administering the active ingredients in a sufficient dosage for therapeutic effect, one such formulation being: four parts of bacterial lysate and one part of N-acetyl D-glucosamine. Excipients can include one or more of, maltodextrin; xanthan gum; acesulfam K; lemon powder and a flavoring, e.g., juice; Mannitol TL-32-04, Microcrystalline Cellulose and Carrageenan, Fructose, PVP-XL TL-11-04, Gellan Gum, Citrus TL 1-04, Orange TL 19-04, Sucrolose TL-13-04, and Mg ST TL-13-04.

16 Claims, No Drawings

OTHER PUBLICATIONS

Liam O'Mahony, Jane McCarthy, et al; *Lactobacillus* and *Bifidobacterium* in Irritable Bowel Syndrome: Symptom Responses and Relationship to Cytokine Profiles; Gastroenterology 2005; 128:541-551.

Dong Hyun Sinn, Ji Hyun Song, et al; Therapeutic Effect of *Lactobacillus acidophilus*-SDC 2012, 2013 in Patients with Irritable Bowel Syndrome (Abstract).

R. Tormo Carnicer, D. Infante Pina, et al; Efecto de la ingesta de leche fermentada con *Lactobacillus casei* DN-114 001 sobre la flora intestinal; An Pediatr (Barc) 2006; 65(5): 448-53.

Nana Valeur, Peter Engel, et al; Colonization and Immunomodulation by *Lactobacillus reuteri* ATCC 55730 in the Human Gastrointestinal Tract; Applied and Environmental Microbiology, Feb. 2004, p. 1176-1181.

Peter Van Baarlen, Freddy J. Troost, et al; Differential NF-kB pathways induction by *Lactobacillus plantarum* in the duodenum of healthy humans correlating with immune tolerance; PNAS, Feb. 17, 2009, vol. 106, No. 7, pp. 2371-2376.

N. Vendt, H. Grunberg, et al; Growth during the first 6 months of life in infants using formula enriched with *Lactobacillus rhamnosus* GG: double-blind, randomized trial; Journal of Human Nutrition and Dietetics, Voll 19, Issue 1, pp. 51-58, Feb. 2006 (Abstract).

* cited by examiner

QUALITY OF LIFE OF HEPATITIS C PATIENTS WITH A FORMULATION FOR ADMINISTRATION TO THE ORAL MUCOSA INCLUDING FREEZE DRIED LYSATE OF SELECTED *LACTOBACILLUS* OR *BIFIDOBACTERIUM* SPECIES AND N-ACETYL D-GLUCOSAMINE

PRIORITY CLAIM

This application is a continuation in part application of application Ser. No. 13/180,779 filed on Jul. 12, 2011, which claims priority of application Ser. No. 11/508,633 filed on Aug. 22, 2006, which was issued on Aug. 30, 2011 with patent number U.S. Pat. No. 8,007,783 and the contents of which are incorporated herein in their entirety by reference.

BACKGROUND

*Lactobacillus reuteri* is a heterofermentative bacterium that resides in the gastrointestinal tract of humans and animals. It is widely used as a dietary supplement. Valeur et al. show that *L. reuteri* colonized human gastrointestinal tract and positively modulated local immune cell populations as consequence of oral intake of *L. reuteri* tablets (Valeur et al. Colonization and Immunomodulation by *Lactobacillus reuteri* ATCC 55730 in the human gastrointestinal tract. Appl. Environ/Microbiol. 2004 February; 70(2):1176-1181).

*Lactobacillus plantarum* is another probiotic bacterium. Klarin et al. show that *L. plantarum* is capable of surviving the passage from the stomach to the rectum and to adhere to the rectal mucosa also in patients treated with antibiotics. (Klarin et al. Adhesion of the probiotic bacterium *Lactobacillus plantarum* 299 on the gut mucosa in critically ill patients: a randomized open trial. Crit. Care 2005; 9(3): R285-293). Qin et al. studied the effects of enteral feeding of *L. plantarum* on the gut permeability and septic complications in the patients with acute pancreatitis. Enteral feeding of *L. plantarum* attenuated disease severity and improved the intestinal permeability. (Qin, H. L et al. Effect of *Lactobacillus plantarum* enteral feeding on the gut permeability and septic complications in the patients with acute pancreatic. Eur. J. CLin. Nutr. 2008 Jul; 62(7): 923-30). Hirose et al. show that heat-killed *L. plantarum* augments acquired immunity in healthy subjects. (Hirose, Y. et al. Daily intake of heat-killed *Lactobacillus plantarum* L-137 augments acquired immunity in healthy adults. J. Nutr. 2006 December; 136(12):3069-73). Van Baarlen et al. describe in vivo immune responses in duodenum of healthy humans after consumption of *L. plantarum* (van Baarlen P. et al. 2009. Differential NF-kB pathways induction by *Lactobacillus plantarum* in the duodenum of healthy humans correlating with immune tolerance. Proc. Natl. Acad. Sci USA 2009. Feb. 17; 106(7): 2371-2376). Klarin et al. show that use of *Lactobacillus plantarum* reduces pathogenic bacterial load in the oropharynx of thracheally intubated, mechanically ventilated, critically ill patients. (Klarin et al. Use of the probiotic *Lactobacillus plantarum* 299 to reduce pathogenic bacteria in the oropharynx of intubated patients: a randomized controlled open pilot study. Crit. Care 2008, 12: R136).

Yet another probiotic bacterium is *Lactobacillus rhamnosus* GG. Vendt et al. showed that children fed with *L. rhamnosus* GG-enriched formula grew better than those fed with regular formula. (Vendt, N. et al. Growth during the first 6 months of life in infants using formula enriched with *Lactobacillus rhamnosus* GG: double-blind, randomized trial. J. Hum. Nutr. Diet. 2006 February; 19(1): 51-8). Another study shows that oral administration of *Lactobacillus rhamnosus* GG supplementation has a positive impact on *Helicobacterium pylori* therapy related side-effects and on overall treatment tolerability. (Armuzzi A. et al. Aliment Pharmacol Ther. 2001. February; 15(2): 163-9. Arvola et al. showed that oral intake of *Lactobacillus* GG reduced antibiotic associated diarrhea in children with respiratory infections. (Arvola T. et al. Prophylactic *Lactobacillus* GG reduces antibiotic associated diarrhea in children with respiratory infections: a randomized study. Pediatrics. 1999 November; 104(5): e64)

*Lactobacillus casei* is another probiotic bacterium that has been shown to have potential to enhance human natural killer cell activity when administered orally in the form of fermented milk. (Takeda K. et al. 2006, Clin. Exp. Immunol. October 146(1):109-115.) Takagi et al. showed that *L. casei* may be associated with tumor suppression (Takagi A. et al. 2008. J. Gastroenterol. 43(9):661-669). Aso et al. demonstrated preventive effect of *L. casei* preparation on the recurrence of superficial bladder cancer in a double-blind trial. (Aso. Y etala. 1995. Eur Urol. 27(2): 104-9.) Tormo Carnicer et al. showed that *L. casei* survives in the gastrointestinal tract and it affects on secretory immunoglobulin levels when orally taken. (Tormo Carnicer, R. et al. 2006. Intake of fermented milk containing *Lactobacillus casei* DN-114001 and its effect on gut flora. An. Pediatr (Barc). November 65(5):448-53.). Cobo Santz et al. demonstrated also that children receiving *L. casei* fermented milk has lower tendency and reduction of duration to incidence of infectious diseases. (Cobo Sanz J M. Et al. 2006. Nutr Hosp. July-0August; 21(4): 547-51). Beausoleil et al. show that fermented milk combining *Lactobacillus acidophilus* and *L. casei* prevent antibiotic-associated diarrhea. (Beausoleil et al. 2007. Effect of a fermented milk combining *Lactobacillus acidophilus* CL1285 and *Lactobacillus casei* in the prevention of antibiotic-associated diarrhea: A randomized, double-blind, placebo-controlled trial. Can J. Gastroenterol. November 21(11):732-736.)

*Lactobacillus acidophilus* strains have been shown to be beneficial for patients suffering of irritable bowel syndrome (Sinn D. H. et al 2008. Therapeutic effect of *Lactobacillus acidophilus*-SDC 2012, 2013 in patients with irritable bowel syndrome. Dig Dis Sci. October 53 (10) 2714-8). Drago et al. showed a treatment of bacterial vaginosis with vaginal douche containing a strain of *L. acidophilus* to restore a normal vaginal environment. (Drago L. et al. 2007 Activity of a *Lactobacillus acidophilus*-based douche for the treatment of bacterial vaginosis. J. Altern. Complement. Med. May 13(4): 435-8.). Danducci F. et al showed that lyophilized and inactivated culture of *Lactobacillus acidophilus* increased *Helicobacter pylori* eradication in patients. (Danducci F. 2000. A lyophilized and inactivated culture of *Lactobacillus acidophilus* increases *Helicobacter pylori* eradication rates. Aliment Pharmacol. Ther. 2000 Dec. 14 (12): 1625-9).

*Bifidobacterium infantis* is a probiotic bacterium that inhabits in intestine of both infants and in adults. O'Mahony et al. showed that oral intake of *B. infantis* alleviated symptoms of irritable bowel syndrome. (O'Mahony et al. 2005. *Lactobacillus* and *Bifidobacterium* in irritable bowel syndrome: symptom responses and relationship to cytokine profiles. Gastroenterology March; 128(3); 541-51). Some indications of reduced occurrence of nectortising enterocolitis has been found by providing live *B. infantis* bacteria to newborns (Hoyos A B. 1999 Reduced incidence of necrotizing enterocolitis associated with enteral administration of *Lactobacillus acidophilus* and *Bifidobacterium* infantis to neonates in an intensive care unit. Int. J. Infect. Dis. Summer; 3(4): 197-202.). Similarly, there are indications that oral administration of live *B. infantis* may be an effective treatment for acute watery diarrhea (Vivatvakin B. 2006. J. Med Assoc.Thai. September; 89 Suppl 3:S126-133.).

*Bifidobacterium longum* has been shown to have potential to alleviate symptoms of ulcerative colitis (Furrie E. 2005 Synbiotic therapy (*Bidifidobacteirum longum*/Synergy 1) initiates resolution of inflammation in patients with active ulcerative colitis: a randomized controlled pilot trial. Gut 2005 February; 54(2):242-249.). deVrese et al show that oral intake of *Lactobacillus gasseri, Bifidobacterium longun* and *Bifidobacterium bifidum* shorten common cold episodes and reduce the severity of the symptoms. (deVrese M. et al. 2005. Effect of *Lactoballius gasseri* PA 16/8, *Bifidobacteruim longum* sP07/3. B. bifidum MF 20/5 on common cold episodes: a double blind, randomized, controlled trial. Clin. Nutr. August; 24(4): 481-91). There is some evidence that bifidobacteria may affect immune response to poliovirus vaccination of infants. Mullie et al. found that antipoliovirus response was triggered with a fermented formula that contained *Bifidobacterium longum, B. infantis* and *B. breve*. (Mullie C. 2004. Increased poliovirus-specific intestinal antibody response coincides with promotion of *Bifidobacterium longum-infantis* and *Bifidobacterium breve* in infants: a randomized, double-blind, placebo-controlled trial. Pediatr. Res November, 56(5): 791-5). Araki et al. demonstrated that oral administration of a *Bifidobacterium breve*-strain significantly decreased rotavirus shedding in stool samples and prevented rotavirus infection. (Araki K. et al. 1999. Kansenshogaku Casshi April; 73(4): 305-310).

U.S. Pat. No. 5,716,615 discloses a pharmaceutical composition containing at least two different lyophilized viable bacteria for treatment of chronic hepatitis following C virus infection.

N-acetyl-glucosamine (NAG) is a compound that exists naturally in the body. In various forms, this compound has been studied for its potential in alleviating some of the conditions associated with several diseases including osteoarthritis, inflammatory bowel disease and Crohn's disease and the inflammatory response in peritonitis (Gardiner, Dietary N-acetylglucosamine(GlcNAc): Absorption, Distribution, Metabolism, Excretion and Biological Activity, Glyco-Science and Nutrition (2000) 1(9):1-3; Salvatore et al., A pilot Study of N-acetyl-glucosamine, a nutritional substrate for glycosaminoglycan synthesis in paediatric chronic inflammatory bowel disease, Alimentary Pharmacology and Therapeutics (2000) 14(12):1567-1579). GMDP (N-acetyl-D-glucosaminyl(beta.-1-4)-N-Acetyl-muramyl-L-ananyl-D-isoglutamine) in combination with NAG has been suggested as a treatment for Hepatitis C (U.S. Pat. No. 6,281,191).

In U.S. Pat. No. 8,007,783 we disclosed a method to treat hepatitis patients with a formulation that consists of lysate of freeze dried *Lactobacillus delbrueckii* subsp. Bulgaricus with N-acetyl glucosamine. Here we expand the method to formulations consisting of lysates of other freeze dried bacterial strains in combination of NAG.

SUMMARY

Disclosed are quick dissolve tablets, each including lysate of freeze dried *Lactobacillus acidophilus, L. reuteri, L. casei, L. plantarum, L. rhamonosus* GG, *Bifidobacterium breve, B. infantis, B. bifidum*, or *B. longum* and N-acetyl-glucosamine (NAG), as well as excipients, for oral mucosal administration. Any formulation suitable for oral mucosal administration can be employed for administering the active ingredients in a sufficient dosage for therapeutic effect, one such formulation being: 50 mg of lysate of freeze dried *Lactobacillus acidophilus, L. reuteri, L. casei, L. plantarum, L. rhamonosus,* *Bifidobacterium breve, B. infantis, B. bifidum* or *B. longum* and 10 mg of N-acetyl D-glucosamine (NAG).

Preferred excipients are maltodextrin; xanthan gum; acesulfam K; lemon powder and a flavoring, e.g., juice. When prepared as described herein, a tablet is generated which dissolves in the mouth in 30 to 45 seconds, although any tablet or formulation capable of dissolving on the oral mucosa in less than about one minute is acceptable.

An object of this invention is to provide a method of treating Hepatitis C infected patients, consisting of: administering to the oral mucosa a formulation consisting of active ingredients being a lysate of freeze dried *Lactobacillus casei, Lactobacillus plantarum, Lactobacillus reuteri, Lactobacillus rhamnosis* GG, *Lactobacillus acidophilus, Bifidobacterium bifidium, Bifidobacterium longum, Bifidobacterium infantis* or *Bifidobacterium breve* and N-acetyl-glucosamine formulated so as to dissolve on the oral mucosa and release the active ingredients in less than about one minute following administration.

Another object of this invention is to provide a formulation to treat Hepatitis C infected patients, said formulation having active ingredients consisting essentially of: a lysate of freeze dried *Lactobacillus reuteri, Lactobacillus casei, Lactobacillus plantarum, Lactobacillus rhamnosus* GG, *Lactobacillus acidophilus, Bifidobacterium bifidium, Bifidobacterium longum, Bifidobacterium infantis* or *Bifidobactrium breve* and N-acetyl-glucosamine; and said formulation dissolving on oral mucosa and release the active ingredients in less than about one minute following administration Clinical trials are underway to determine the effect of these formulations on quality of life for Hepatitis C infected patients. The SF-36 score measures the quality of life for patients, based on a self-administered scoring system that includes eight independent scales and two main dimensions. It has been widely used and validated. An increase in quality of life of two points or more on the SF-36 scoring system, over the course of six months of administration of the formulation, is scored as improvement in the clinical trial.

DETAILED DESCRIPTION

In order to generate the formulation described herein suitable for therapy, which is capable of dissolving on the oral mucosa in less than about one minute and releasing the active ingredients, the following exemplary procedure may be followed, although there are a number of other processes which could also generate a suitable formulation. The process consists of three steps of processing the active ingredients and two steps involving formulation and tablet making.

1. Active Ingredient Process

Fermentation

Cells of *Lactobacillus acidophilus, L. reuteri, L. casei, L. plantarum, L. rhamonosus* GG, *Bifidobacterium breve, B. infantis, B. bifidum*, or *B. longum* are fermented in 500 L of an appropriate media for approximately 120 hours.

Cell Isolation

The 500 L of broth is centrifuged and the resultant cell mass is washed three times with DI water. This produces approximately 60 kg of wet cell mass.

Lysing and Purification

The wet cell mass is reconstituted and the pH is adjusted to 6.8-7.0. Lysozyme chloride (extracted from hen egg whites) is added to make a solution with a concentration of 500 ppm of lysozyme chloride. The slurry is agitated and the temperature is maintained at 40-50° C. for 24 hours. After lysing, the active components are in the liquid phase. This liquid material containing the water soluble active components is recovered through centrifugation to remove the solid material, and then washed three times with DI water. The resultant mixture is frozen in pellets and the remaining solid material in the centrifuge is discarded.

2. Formulation and Tableting

The frozen pellets are freeze dried to form a dry powder and milled, if necessary. This material is blended with excipients and N-acetyl D-glucosamine HCl (NAG) to form a mixture of 52 mg lysed *Lactobacillus acidophilus, L. reuteri, L. casei, L. plantarum, L. rhamonosus* GG, *Bifidobacterium breve, B. infantis, B. bifidum* or *B. longum* and 13 mg NAG, per pellet. Purified water is added to the blended mixture in preparation for making the quick dissolve tablets. Approximately 180 mg of the solution of bacterial lysate, NAG, and excipients (e.g., maltodextrin; xanthan gum; acesulfam K; lemon powder and a flavoring) are added to preformed 2 ml wells in PVC plastic stock and then placed in a lyophilization chamber. After lyophilization, the PVC plate is removed and lid stock is applied to form a sealed product.

The tablet is gray, in the shape of the plastic well, with a mirror finish on the side next to the plastic stock and rough appearance on the top. When placed on the tongue, and not chewed or swallowed, the tablet dissolves in 30-45 seconds.

Another exemplary formulation for a quick dissolve tablet for administering the active ingredients through the oral mucosa includes the following ingredients in the following proportions:

TABLE I

| | |
|---|---|
| Mannitol TL-32-04 | 52.8% |
| Microcrystalline Cellulose and Carrageenan | 15.0% |
| Fructose | 12.5% |
| PVP-XL TL-11-04 | 5.0% |
| Bacterial lysate (four parts); NAG (one part) | 9.1% |
| Gellan Gum | 0.5% |
| Citrus TL 1-04 | 3.0% |
| Orange TL 19-04 | 1.0% |
| Sucrolose TL-13-04 | 0.5% |
| MgST TL-13-04 | 0.6% |

It can be formulated according to methods known to those skilled in the art.

It should be understood that the terms, expressions, procedures and examples herein are exemplary only, and not limiting, and that the scope of the invention is defined only in the claims which follow, and includes all equivalents of the subject matter of the claims.

What is claimed is:

1. A formulation to treat Hepatitis C infected patients, active ingredients of said formulation consisting essentially of:
    a freeze dried lysate of *Lactobacillus reuteri, Lactobacillus casei, Lactobacillus plantarum, Lactobacillus rhamnosus* GG, *Lactobacillus acidophilus, Bifidobacterium bifidium, Bifidobacterium longum, Bifidobacterium infantis* or *Bifidobactrium breve* and N-acetyl-glucosamine; and
    said formulation dissolving on oral mucosa and releasing the active ingredients in less than about one minute following administration.

2. The formulation of claim 1, wherein the formulation has four parts of the lysate and one part of N-acetyl D-glucosamine.

3. The formulation of claim 2, wherein the formulation further has excipients.

4. The formulation of claim 3, wherein the excipients are selected from the group consisting of maltodextrin, xanthan gum, acesulfame K, lemon powder and a flavoring.

5. The formulation of claim 3, wherein the excipients are selected from the group consisting of Mannitol, Microcrystalline Cellulose and Carrageenan, Fructose, PVP, Gellan Gum, Citrus-flavor, Orange-flavor, Sucralose, and Mg-stearate.

6. The formulation of claim 1, wherein treating patients results into an improvement in quality of life indicated by a two point or greater improvement in SF-36 scores.

7. The formulation of claim 1, wherein the formulation is a tablet and dissolves within 30 to 45 seconds following administration.

8. The formulation of claim 7 wherein the tablet consists of 9.1% of active ingredients, 52.8% of mannitol, 15.0% of microcrystalline cellulose and carrageenan, 12.5% of fructose, 5.0% of PVP, 0.5% of Gellan Gum, 3.0% of Citrus-flavor, 1.0% Orange-flavor 0.5% Sucralose and 0.6% of Mg-stearate.

9. The formulation of claim 7, wherein treating patients results in an improvement in quality of life of Hepatis C patients indicated by a two point or greater improvement in SF-36 scores.

10. A method of treating Hepatitis C infected patients, consisting of:
    administering to the oral mucosa a formulation according to claim 1.

11. The method of claim 10, wherein the formulation includes four parts of the lysate and one part of N-acetyl D-glucosamine.

12. The method of claim 11, wherein the formulation further includes excipients.

13. The method of claim 12, wherein the excipients are selected from the group consisting of maltodextrin, xanthan gum, acesulfam K, lemon powder, and a flavoring.

14. The method of claim 12, wherein the excipients are selected from the group consisting of Mannitol TL-32-04, Microcrystalline Cellulose and Carrageenan, Fructose, PVP, Gellan Gum, Citrus-flavor, Orange-flavor, Sucralose, and Mg-stearate.

15. The method of claim 10, wherein quality of life of patients increases by a two point or greater improvement in SF-36 scores.

16. The method of claim 10, wherein the formulation dissolves within 30 to 45 seconds following administration.

* * * * *